(12) United States Patent
Kwong

(10) Patent No.: US 12,220,107 B2
(45) Date of Patent: Feb. 11, 2025

(54) SPECULUM WITH ATTACHMENT MEANS

(71) Applicant: GWMV LIMITED, London (GB)

(72) Inventor: Tsong Kwong, London (GB)

(73) Assignee: AUDELATION LIMITED, London (GB)

( * ) Notice: Subject to any disclaimer, the term of this patent is extended or adjusted under 35 U.S.C. 154(b) by 734 days.

(21) Appl. No.: 16/608,579

(22) PCT Filed: Apr. 25, 2018

(86) PCT No.: PCT/GB2018/051084
§ 371 (c)(1),
(2) Date: Oct. 25, 2019

(87) PCT Pub. No.: WO2018/197870
PCT Pub. Date: Nov. 1, 2018

(65) Prior Publication Data
US 2020/0178776 A1    Jun. 11, 2020

(30) Foreign Application Priority Data

Apr. 25, 2017 (GB) ..................................... 1706497

(51) Int. Cl.
*A61B 1/04*    (2006.01)
*A61B 1/00*    (2006.01)
*A61B 1/227*   (2006.01)

(52) U.S. Cl.
CPC .......... *A61B 1/042* (2013.01); *A61B 1/00105* (2013.01); *A61B 1/0014* (2013.01); *A61B 1/227* (2013.01)

(58) Field of Classification Search
CPC ... A61B 1/042; A61B 1/00105; A61B 1/0014; A61B 1/227; A61B 1/24; A61B 1/32
See application file for complete search history.

(56) References Cited

U.S. PATENT DOCUMENTS 3,848,587 A * 11/1974 McDonald ............... A61B 1/07
600/187
4,006,738 A *  2/1977 Moore ..................... A61B 1/07
385/119
(Continued)

FOREIGN PATENT DOCUMENTS

CN         2108937 U      7/1992
CN       201628809 U     11/2010
(Continued)

OTHER PUBLICATIONS

World Intellectual Property Organization, International Search Report for International Application No. PCT/GB2018051084, mailed Aug. 8, 2018, 3 total pages.

(Continued)

*Primary Examiner* — Anh Tuan T Nguyen
*Assistant Examiner* — Shankar Raj Ghimire
(74) *Attorney, Agent, or Firm* — SoCal IP Law Group LLP; Mark Andrew Goldstein

(57) ABSTRACT

The invention relates to a device comprising a digital camera, a speculum and an attachment means for attaching the camera to the speculum, wherein the speculum defines a first end with a first opening, and a second end with a second opening; and wherein the attachment means is attached to the first end of the speculum and the camera is has a first position substantially in the plane of the first opening such that it can view a region beyond the second opening. The device may be an otoscope and may be used in the visualization and treatment of the ear canal.

13 Claims, 9 Drawing Sheets

(56) References Cited

U.S. PATENT DOCUMENTS

| | | | |
|---|---|---|---|
| 5,363,839 A | | 11/1994 | Lankford |
| 5,658,235 A | | 8/1997 | Priest et al. |
| 6,106,457 A | * | 8/2000 | Perkins ................ A61B 5/0013 |
| | | | 600/172 |
| 6,319,199 B1 | | 11/2001 | Sheehan et al. |
| 10,939,813 B2 | | 3/2021 | Holland |
| 2005/0171399 A1 | | 8/2005 | Rich et al. |
| 2007/0261494 A1 | * | 11/2007 | Fuller ................... A61B 8/445 |
| | | | 73/620 |
| 2011/0295073 A1 | | 12/2011 | Truong et al. |
| 2012/0218514 A1 | * | 8/2012 | Kwong ............. A61B 1/00105 |
| | | | 428/397 |
| 2012/0245422 A1 | | 9/2012 | Hasbun |
| 2013/0023914 A1 | | 1/2013 | Truong et al. |
| 2013/0107109 A1 | * | 5/2013 | Yang ...................... H04N 23/51 |
| | | | 359/827 |
| 2013/0178707 A1 | * | 7/2013 | Kwong .................... A61B 1/06 |
| | | | 600/200 |
| 2013/0300919 A1 | * | 11/2013 | Fletcher ............ A61B 1/00052 |
| | | | 348/360 |
| 2014/0142390 A1 | | 5/2014 | Bromwich |
| 2016/0249805 A1 | | 9/2016 | Salvati |
| 2016/0374546 A1 | * | 12/2016 | Berbee ..................... A61B 1/05 |
| | | | 600/109 |
| 2017/0239091 A1 | * | 8/2017 | Franz ................... A61B 1/0676 |
| 2017/0273539 A1 | * | 9/2017 | Law ........................ A61B 1/04 |
| 2017/0303857 A1 | * | 10/2017 | Perkins ............. A61B 1/00052 |
| 2018/0168440 A1 | * | 6/2018 | Das ...................... A61B 5/0082 |
| 2018/0333041 A1 | * | 11/2018 | Lo ...................... A61B 1/00126 |
| 2020/0337544 A1 | * | 10/2020 | Goldfarb .............. A61B 1/0669 |
| 2021/0068645 A1 | * | 3/2021 | Elson ..................... A61B 1/042 |

FOREIGN PATENT DOCUMENTS

| | | | |
|---|---|---|---|
| EP | 2 664 266 A1 | 11/2013 | |
| GB | 2 534 019 A | 7/2016 | |
| KR | 2013 0049704 A | 5/2013 | |
| TW | M520876 U | 5/2016 | |
| WO | WO-02056756 A2 * | 7/2002 | ......... A61B 1/00016 |
| WO | 2005050156 A2 | 6/2005 | |
| WO | 2007115225 A2 | 10/2007 | |
| WO | 2018197870 A1 | 11/2018 | |
| WO | 2019116024 A1 | 6/2019 | |

OTHER PUBLICATIONS

United Kingdom Intellectual Property Office, Search Report for Application No. GB1806767.8, mailed Sep. 25, 2018, 4 total pages.

China National Intellectual Property Administration, Office Action for Application No. 2018800412597, mail date Nov. 3, 2021, 21 total pages with English translation.

Firefly Global, Extended Video Otoscope Veterinary Specula, web page https://web.archive.org/web/20160328074758/https://fireflyglobal.com/veterinary-video-otoscope-specula-es108/, last accessed Feb. 2, 2021, 3 total pages.

* cited by examiner

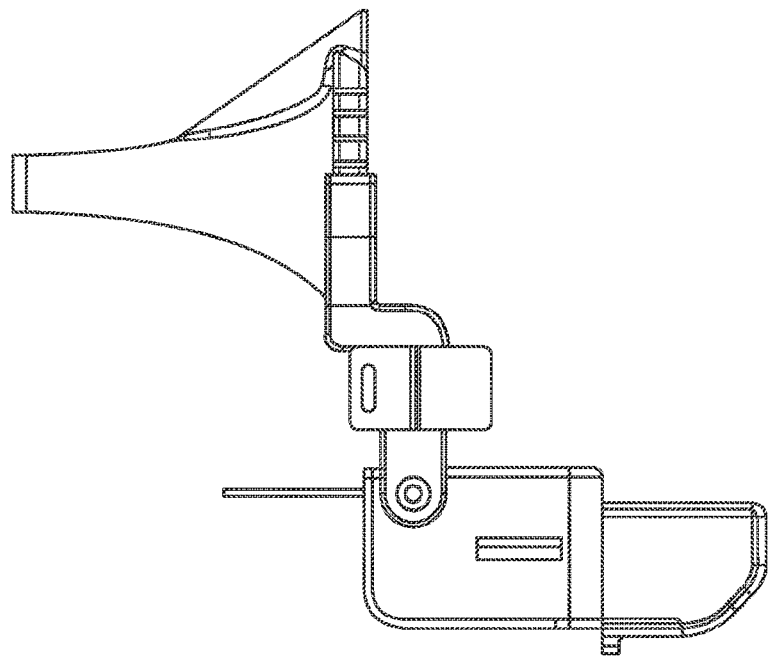
Figure 3c
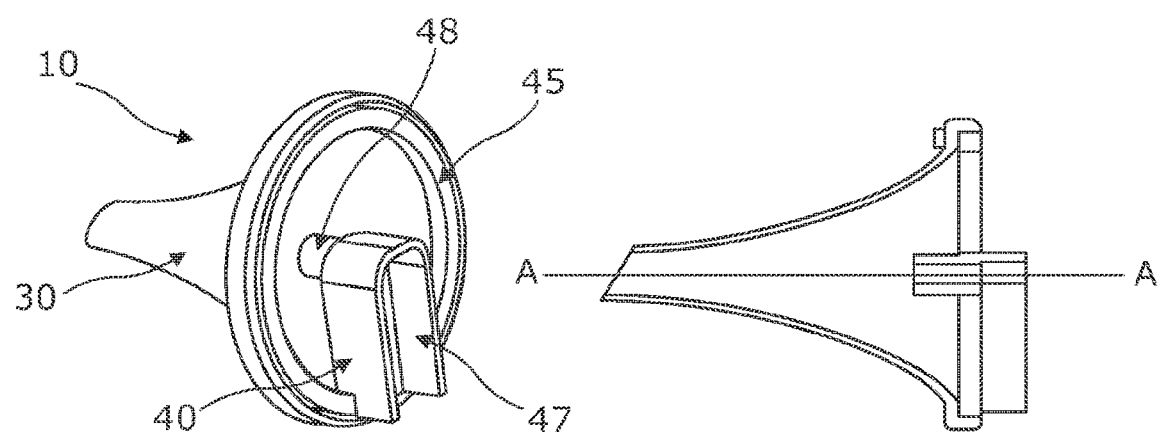
Figure 4a
Figure 4b

SPECULUM WITH ATTACHMENT MEANS

RELATED APPLICATION INFORMATION

This patent claims priority from International PCT Patent Application No. PCT/GB2018/051084, filed Apr. 25, 2018 entitled, "NEW PRODUCT", which claims priority to United Kingdom Patent Application No. 1706497.3, filed Apr. 25, 2017 entitled, "NEW PRODUCT", all of which are incorporated herein by reference in their entirety.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

FIELD OF THE INVENTION

The present invention relates to a new product, in particular a medical product and more particularly a medical device for use in the field of otoscopy and visualization of the outer ear canal.

BACKGROUND OF THE INVENTION

The ears of humans and other animals can require examination and/or treatment from time to time, or when the patient is afflicted with a particular disease. It is especially common for patients to require removal of earwax, which is also known as cerumen, using techniques such as aural microsuction.

As well as being useful in the restoration of a patient's hearing and for general aural health, the removal of earwax is necessary in audiological assessments, and in the fitting and maintenance of hearing aids. The removal of wax or foreign bodies from the ear of a patient is the most common outpatient appointment in the world.

The overall process of removing wax or a foreign body from a patient's ear is typically composed of two procedures: ear canal inspection (otoscopy); and removal of the wax or foreign body using microsuction and/or tools, such as wax hooks and/or Jobson Home Probes.

Examination and treatment of the outer ear canal can be performed by a variety of devices, such as microscopes, loupe glasses, rigid endoscopes and conventional otoscopes. However, each of these types of device has its own problems.

Ear microscopes are typically preferred for the removal of wax or a foreign body from a patient's ear. These devices allow for direct vision of the ear canal. Ear microscopes are typically freestanding. However, ear microscopes are large and not portable, occupying a lot of clinic space. Ear microscopes are also considerably expensive. In addition, ear microscopes do not allow the patient to move position during examination and/or treatment, and a microscope can require frequent readjustment during an examination or treatment to keep the desired area in view.

Loupe glasses are glasses with small, magnifying lenses that are very portable and allow visualization of the ear canal. Loupe glasses suffer from the fact that they need to be bespoke for each clinician, to fit their eye dimensions and prescription. In addition, loupe glasses provide a fixed focus, magnification and viewpoint, meaning that the clinician has to move their head to produce different views. This requirement for movement can make clinicians nauseous. Loupe glasses commonly require illumination and are therefore used with additional headwear and a large battery pack to provide a light source. A clinician using loupe glasses must maneuver around the patient to keep the area of examination and/or treatment in view.

Rigid endoscopes and conventional otoscopes offer visualization of the ear canal but give rise to problems including restriction or even prevention of the access of instruments required to perform treatments such as aural microsuction.

Rigid endoscopes require a lighting source to be present within the ear canal. Such lighting sources typically generate heat, which puts the patient at risk of receiving burns. Furthermore, in use the endoscope extends into the ear canal, restricting the movement of instruments and providing an increased risk of ear drum perforation. The insertion of rigid endoscopes into the ear canal also means that they require sterilization after each use to prevent cross-contamination between patients.

Conventional otoscopes are frequently used to physically examine the outer ear canal. Otoscopes typically comprise a handle and viewing system, wherein the viewing system holds a light source and a tip. Otoscopes are usually used with disposable ear specula to cover the tip and prevent cross-contamination between patients. However, having a speculum attached to, for example screwed on to, and covering the tip prevents the passage of instruments into the ear canal to perform treatments, such as earwax removal. The presence of the otoscope in the outer ear canal for visualization purposes restricts or prevents access to the ear canal with instruments.

SUMMARY

The inventor has realized that the portability of ear microscopes prevents these devices being used outside of the clinic. This presents a particular issue because patients must be referred to a specialist that has the required equipment. Furthermore, the lack of portability of the equipment means that treatment cannot easily be performed on patients that are immobile.

In addition improved visualization of the outer ear canal and ear drum whilst also allowing access for instruments that are required to be inserted into the outer ear canal is an aim of this invention.

Therefore, the inventor has determined a need for an otoscope that is portable to enable clinicians to perform procedures such as earwax removal outside of the clinic and that allows visualization of the outer ear canal and ear drum without preventing, and ideally without unduly restricting, access of instruments.

The present invention provides, in a first aspect, a device comprising a digital camera, a speculum and an attachment means for attaching the camera to the speculum, wherein:
 the speculum defines a first end with a first opening, and a second end with a second opening; and wherein the attachment means is attached to the first end of the speculum;
 the camera has a first position substantially in the plane of the first opening such that it can view a region beyond the second opening.

The present invention provides a device comprising a speculum and an attachment means for attaching a camera to the speculum, wherein:

the speculum defines a first end with a first opening, and a second end with a second opening; and wherein the attachment means is attached to the first end of the speculum; the attachment means is configured such that in use the camera has a first position substantially in the plane of the first opening such that it can view a region beyond the second opening.

The device may include a camera, preferably a digital camera.

The present invention provides a device comprising a speculum and an attachment means for attaching a camera to the speculum, wherein:

the speculum defines a first end with a first opening, and a second end with a second opening; and wherein the attachment means is attached to the first end of the speculum;

the attachment means is configured such that in use the camera has a first position such that it can view a region beyond the second opening;

the first position being such that in use the view of the region beyond the second opening is not obscured by objects passing between the camera and the first opening of the speculum.

The first position being such that in use the view of the region beyond the second opening is not obscured by objects passing between the camera and the first opening of the speculum may be achieved by the attachment means being configured to position the camera in the first position close to the first opening of the speculum, for examples substantially in the plane of the first opening of the speculum.

The device may include a camera, preferably a digital camera.

The device may be a medical device, preferably an otoscope.

The inventor has devised a portable otoscope that is capable of use in a multitude of different scenarios. The otoscope allows visualization of the outer ear canal and ear drum without preventing, and ideally without unduly restricting, access of instruments. The otoscope of the present invention is simply and low cost.

The present invention is directed to improving the construction of otoscopes and its primary function is to allow digital viewing of the outer canal and ear drum. The inventor proposes the use of a handle-less otoscope. We describe in the present invention integration with a digital camera and ear speculum and a novel mechanism to avoid wax and debris contamination. Typically otoscopes require the construction of a handle to be able to hold a speculum—however in this invention the inventor describes how an otoscopy can be performed by holding the speculum alone.

In one embodiment the camera is configured to be displaced. In one embodiment the attachment means is configured to be displaced. This allows the camera to be displaced. Such displacement may aid the access and/or removal of the instrument. In particular, such displacement may help to prevent contaminated instruments from contaminating parts of the otoscope that are not disposable, such as the camera.

The otoscope of the present invention may suitably be used in the process of removing earwax or debris from the outer ear canal.

Accordingly, in a second aspect, the present invention provides a method of using a device according to the first aspect.

According to a third aspect, the present invention provides a method of diagnosing the human or animal with a disease or condition, the method comprising providing a device according to the first aspect and using the device in the process of diagnosing the human or animal body with a disease or condition.

According to a fourth aspect, the present invention provides a method of treating the human or animal body, the method comprising providing a device according to the first aspect and using the device in the process of treating the human or animal body.

DETAILED DESCRIPTION

The device of the invention, which may in a preferred embodiment be an otoscope, is configured to allow an instrument to reach through the first opening and the second opening of the speculum such that the instrument can be operated by a user from beyond the first opening to operate in the region beyond the second opening.

The present invention allows the skilled person to examine and/or perform procedures on the ear of a patient without requiring an ear microscope. The device of the present invention allows the clinician to readily examine and/or perform procedures on the ear of a patient in locations other than a clinic, such as in the patient's home or in a residential care home. The present invention also provides a greater degree of access to the ear canal for instruments than would be possible using a conventional rigid endoscope or conventional otoscope.

Speculum

In one embodiment, the device, which may be an otoscope, comprises a speculum that defines a first end and a second end, wherein the first end comprises a first opening, and wherein the second end comprises a second opening. The first opening and the second opening may be substantially parallel. The first opening may define a larger diameter than the second opening. The center of the first opening and the center of the second opening may define a central axis.

The first opening may also be referred to as the mouth in this application.

In one embodiment, the speculum is an ear speculum. The skilled person will appreciate that an ear speculum is different from other types of speculum, such as a nasal, rectal or vaginal speculum. Ear specula are typically hollow, and frustoconical or funnel-shaped, with a first end with a first opening and a second end with a second opening. A side wall extends between the first opening and the second opening. The side wall of the ear specula may be curved as it extends between the first opening and the second opening. Alternatively the side wall of the ear speculum may be straight.

In one embodiment, speculum of the device of the invention is a conventional speculum widely available and universally accepted.

In one embodiment, the first opening is substantially circular or substantially oval. The speculum may comprise a projection to facilitate the insertion of tools. The projection may expand the circumference of the first end and/or expand the circumference of the first opening of the speculum. The projection may extend inwardly from the circumference of the first end towards the centre of the first opening. The projection may be of any suitable shape, for example ring shaped, hook shaped or in the form of an open of closed channel.

The speculum may comprise a channel to facilitate the insertion of tools. The channel may extend from the first opening towards or to the second opening of the speculum.

The channel may extend along the side wall of the speculum, preferably along an inner surface of the side wall. Alternatively the channel may expand or distort the shape of the speculum and extend along an outer surface of the side wall, or form part of the side wall.

The channel may also be referred to in this application as a projection, tunnel or bulge.

In one embodiment, the inner diameter of the first opening of the speculum is 10 mm or more, such as 15 mm or more, or 20 mm or more. For example, the inner diameter of the first opening of the speculum may be 25 mm or more, such as 30 mm or more, or 40 mm or more, or 50 mm or more. A larger first opening may facilitate the insertion of instruments through the speculum. A larger first opening may also reduce the risk of the camera being contaminated with earwax on an instrument as it is removed from the speculum. In one embodiment the inner diameter of the first opening is 100 mm or less, such as 75 mm or less, or 50 mm or less. For example, the inner diameter of the first opening of the speculum may be 40 mm or less, or 30 mm or less, such as 20 mm or less. In one embodiment, the inner diameter of the first opening of the speculum may be from 10 mm to 100 mm. Preferably, the inner diameter of the first opening of the speculum is from 20 mm to 50 mm.

In one embodiment—the larger first opening may facilitate the insertion of instruments through the speculum and through the smaller second opening. A larger first opening may also reduce the risk of the camera being contaminated with ear wax as the instrument is removed from the speculum.

In one embodiment, the second opening is substantially circular or substantially oval but is not limited to being so e.g. a rectangular/square or triangular second opening may be constructed.

Typically, there are range of specula with a variety of second hole diameters which reflect the variety of sizes of ear canals that the clinicians may encounter. Typically the second hold diameter can be any value between 4-7 mm but is not limited to being to this range Pediatric speculum may have a smaller second hole diameter below 4-7 mm.

In one embodiment the second opening is 10 mm in diameter or less, such as 7 mm in diameter or less, such as 6 mm or less, or 5 mm or less, or 5 mm or less. In one embodiment, the second opening is 4 mm or less, such as 3 mm or less, such as 1 mm. In one embodiment, the second opening is 1 mm in diameter or more, such as 3 mm in diameter or more, or 4 mm or more, or 5 mm or more, or 6 mm or more. For example, the second opening may be 7 mm in diameter or more, such as 10 mm. In one embodiment the second opening is from 1 mm to 10 mm in diameter. Preferably the second opening is from 3 mm to 7 mm in diameter. The most commonly used specula have a second opening that is 6 mm in diameter for in adults and around 3-4 mm in diameter for children.

The first opening defines a larger diameter than the second opening. For example, the diameter of the first opening may be 2 mm or more larger than the second opening, or 5 mm or more, or 10 mm or more, such as 15 mm or more or 20 mm or more larger than the second opening. For example, the diameter of the first opening may be 100 mm or less larger than the second opening, such as 50 mm or less larger than the second opening. In one embodiment, the diameter of the first opening may be from 2 mm to 100 mm larger than the diameter of the second opening. Preferably, the diameter of the first opening is 10 mm to 50 mm larger than the diameter of the second opening. The ratio of the diameter of the first opening to the diameter of the second opening may be 1.1:1 or more, or 1.2:1 or more, or 1.5:1 or more, or 2:1 or more, or 3:1 or more.

There may be no obvious relationship between the diameters of the first and second opening. For example one commercially used speculum has a fixed 35 mm first opening but a range of second openings from 4 to 7 mm.

The first opening and the second opening may be substantially parallel. Substantially parallel may be defined as 90° or less from parallel, 45° or less from parallel, such as 30° or less, or 20° or less, or 10° or less from parallel. The first and second openings may be parallel.

The length of a speculum may be defined by the distance from the first opening to the second opening. The distance from the first opening to the second opening may be 1cm or more, such as 2 cm or more, or 3 cm or more, or 4 cm or more, or 5 cm or more. The distance from the first opening to the second opening may be 10 cm or less, such as 8 cm or less, or 6 cm or less, for example 5 cm or less, or 4 cm or less. The distance from the first opening to the second opening may be from 1 cm to 10 cm. In a preferred embodiment the distance from the first opening to the second opening is from 2 cm to 6 cm.

The first end of the speculum may be held by the clinician in use. For example, a clinician may hold the speculum between their thumb and index finger, or between their thumb, index finger and their middle finger. Therefore in one embodiment the first end of the speculum is robust enough to take pressure from the grip of the clinician.

The attachment means is attached to the first end of the speculum. Therefore, in one embodiment, the first end of the speculum is robust enough to support the weight of the attachment means and camera.

To this end, the wall of the speculum may be thicker at the first end than at the second end. For example, the speculum wall may be 0.5 mm thick or more, such as 1 mm thick or more, or 1.5 mm thick or more at the first end. The speculum wall may be 1 mm thick or less, such as 0.5 mm or less, or 0.25 mm thick or less at the second end. Alternatively or in addition the first end of the speculum may be provided with a lip or a flange extending around the first opening to increase its strength/robustness.

The speculum may suitably be made from a plastic, such as polypropylene, or a metal, such as stainless steel. In one embodiment, the speculum is disposable. In one embodiment, the speculum is able to be autoclaved, boiled, or otherwise sterilized, such as in sterilizing fluid.

Typically the speculum is matte black in color but the present invention is not limited to this and can include speculum of any color, for example speculum that are fully or in part transparent or clear.

The speculum preferred use is for single use and disposable however multi-use speculum that are cleaned/sterilized are not excluded.

Attachment Means

The attachment means is for attaching to the first end of the speculum. The attachment means is attached to the speculum. The attachment means may be unitary with the speculum. The attachment means may therefore be formed as one piece with the speculum.

The attachment means may also be referred to in this application as extension to receive a camera, camera portion, horizontal strut, camera structure, camera system, camera attachment mechanism, camera holding element.

The attachment means comprises an attachment portion for attachment to the first end of the speculum. The attachment means comprises a portion to receive the camera.

The attachment portion may comprise any suitable means for attaching to the speculum such as one or more clips, screws, or male-female engaging parts. The attachment portion may be unitary with the speculum. The attachment portion may therefore be formed as one piece with the speculum.

The attachment portion may suitably comprise a ring to attach to the first end of the speculum. The ring may be configured to fit around the first end of the speculum or fit within the first end of the speculum. For example, the diameter of the ring may be greater or smaller than the first opening. In one embodiment the ring is substantially circular or substantially oval. The ring may include one or more protrusions or recesses that engage with one or more corresponding protrusions or recesses on the first end of the speculum. The ring may press fit around or within the first end of the speculum. The ring does not have to be a complete circle or oval—a portion of the arc of the circle or oval may be missing. For example, the ring may extend for 180° around the central axis or more of the speculum, such as 225° or more, or 270° or more, or 315° or more around the central axis of the speculum.

The invention further provides a device comprising a portion for attachment to a speculum including a portion to receive a camera wherein the portion for attachment to a speculum comprises an arc or ring shaped member configured to fit around or within a speculum and the portion to receive a camera is configured such that in use the camera has a first position substantially in the plane of the first opening such that it can view a region beyond the second opening.

The invention further provides a device comprising a portion for attachment to a speculum including a portion to receive a camera wherein the portion for attachment to a speculum comprises an arc or ring shaped member configured to fit around or within a speculum and the portion to receive a camera is configured such that in use the view of the region beyond the second opening is not obscured by objects passing between the camera and the first opening of the speculum.

The first position being such that in use the view of the region beyond the second opening is not obscured by objects passing between the camera and the first opening of the speculum may be achieved by the attachment portion and/or portion to receive a camera being configured to position the camera in the first position close to the first opening of the speculum, for example substantially in the plane of the first opening of the speculum.

The portion to receive the camera may be mounted on the attachment portion. The portion to receive the camera may be secured to the attachment means by any suitable means. The portion to receive the camera may be unitary with the attachment means. The portion to receive the camera may therefore be formed as one piece with the attachment portion.

The camera has a first position in which it is substantially in the plane of the first opening such that it can view a region beyond the second opening. This position is also referred to in this application as flush with the vertical axis of the specula mouth. Ideally in this first position the camera view is along the central axis of the speculum. The attachment means is preferably configured to position the camera in this first position. The attachment portion may be configured to position the camera in this first position.

The camera may have a second position in which it only extends partly across the first opening. In the second position the camera may not extend across the first opening at all. The attachment means is preferably configured to position the camera in this second position. The attachment portion may be configured to position the camera in this second position.

The attachment means may also act as an infection control measure and can include a structure that is use to protect the camera during use from the instrumentation and debris and wax from patients ears. It may be constructed using transparent materials and not to impede the view of the camera.

The camera may be movable within the portion to receive the camera or a part thereof.

The portion to receive the camera or a part thereof may be configured, for example sized and shaped, such that the camera can slide or telescope between the first and a second position.

Means may be provided to secure the camera in one or both of the first and second positions.

The portion that receives the camera may be pivotally or rotatably secured to the attachment portion such that it can rotate or pivot. This allows the camera to move between the first and a second position.

The portion that receives the camera may be secured to the attachment portion by a hinge. This allows the camera to move between the first and a second position by a hinged movement.

The portion that receives the camera may be secured to the attachment portion by a resilient portion. This allows the camera to move from the first to a second position but return to the first position.

Camera and Lighting System

The device of the present invention, preferably an otoscope, preferably comprises a digital camera that can view a region beyond the second opening. The digital camera may be positioned to view beyond the second opening. The digital camera is preferably positioned to view along the central axis from a position substantially in the plane of the first opening. The digital camera may be positioned to view other than along the central axis.

The attachment means is preferably configured to position the digital camera in this position. The attachment portion may be configured to position the camera in this position.

It will be understood that, in use, the region beyond the second opening will be within the ear canal or ear drum of a patient.

In one embodiment, the camera is a digital camera, particularly a micro-digital camera, such as a charge-coupled device (CCD). Suitable cameras include those that are employed in mobile phones. In a preferred embodiment, the device comprises a micro-digital camera.

In front of the camera may be a single lens or a plurality of lenses that may assist in the focusing of the camera and also create a stable depth of view appropriate for otoscopy and surgical procedures.

The camera may be a fiber optic camera, such as a flexible endoscope.

The device may include a lighting system, for example and electric lighting system.

A lighting system, for example and electric lighting system, can be incorporated within the digital camera.

The lighting system can be comprised of the use of LED's or bulbs that form illumination for the camera. One possible arrangement is a lighting system which is designed to be around the camera. The lighting system can be also be designed so there can be lenses that direct the light into the field of view and that the light from each LED can, by additionality, provide a bright field of view.

The attachment means, in particular the attachment portion or portion to receive a camera, may also provide a focusing means for the LED's and/or the camera.

As already explained, in one embodiment the device is configured to allow the camera to be displaced from the first position. Such displacement may aid the access and/or removal of instruments. In particular, such displacement may help to prevent contaminated instruments from contaminating parts of the device that are not disposable, such as the camera.

The camera therefore has a second position in which it does not extend, or only extends partly, across the first opening. Ideally in the second position the camera is positioned to leave space for instrument access. Ideally in the second position the camera is not positioned to view along the central axis leaving this free for instrument access.

In one embodiment, the device is configured to allow the camera to be displaced from the first position in a plane that is perpendicular to the central axis or parallel to the first opening.

In one embodiment, the device is configured to allow the camera to be displaced from the first position in a plane defined by the central axis or in a plane perpendicular to the first opening.

In one embodiment, the device is configured to allow the camera to retract from the first position along a plane defined by the central axis.

It will be appreciated that any of these options can facilitate the insertion of instruments through the speculum. It will also be appreciated that any of these options reduce the risk of the camera being contaminated with earwax on an instrument as it is removed from the ear through the speculum.

In use, the camera ideally detects along the central axis to allow the best possible view of the ear canal for the clinician.

In use, the camera detects from a position substantially in the plane of the first opening.

Therefore, the camera may be in the plane of the first opening. The camera may be 40 mm or less, 30 mm or less, 20 mm or less, such as 10 mm or less, or 5 mm or less, or 4 mm or less, or 3 mm or less, or 2 mm or less or 1 mm or less, either inside or outside of the plane of the first opening. It will be understood that "inside" the first opening refers to the camera being within the speculum in use. Preferably the first position of the camera is from in line with the first opening to 10 mm or less, or 5 mm or less, or 4 mm or less, or 3 mm or less, or 2 mm or less, or 1 mm or less outside of the plane of the first opening.

Though it is preferred that the camera is in direct line of the central axis of the speculum—for space reasons this may be impractical. We therefore also describe an embodiment where instead of the camera being positioned to view along the central axis, a material/mechanism to reflect light into the camera (which is located elsewhere in the attachment means) such as a mirror, a light pipe, lenses or materials that have reflective properties is provided. Having, for example, a mirror instead of a camera allows the attachment means to be physically smaller than when the camera is mounted for direct vision of the outer ear canal. In such cases software within the system can compensate for issues that can affect the surgical procedure such as orientation.

The positioning of the camera substantially in the plane of the first opening minimizes the possible obstruction of the view by items being passed between the camera and patient. The device of the present invention ensures this is achieved without access of instruments being unduly restricted or even prevented.

A plurality of cameras, preferably digital microcameras, may be provided. The use of more than one camera provides enhanced images such as 3-D images.

In one embodiment the device further comprises a viewing device in communication with the camera. In one embodiment, the viewing device is able to be positioned independently with respect to the camera. For example, the viewing device may be connected to the camera by a cable that is one meter long or more, such as two meters long or more. The viewing device may be connected to the camera wirelessly such as by Bluetooth or across WiFi. The use of a viewing device will allow the patient to freely move their head without affecting the clinician's view of the ear canal. This may provide benefits such as increasing the comfort of the patient, increasing the comfort of the clinician, and providing an improved view of the patient's ear canal in that the clinician's view is less likely to be obscured when either they or the patient moves.

The ability to capture images, through the camera and/or viewing device, is a key benefit allowing users to share with their patient and patient record or with other clinicians for advice, communication or training. The use of a viewing device improves the comfort of both the user and the clinician during use by decoupling patient and clinician positioning, whilst retaining familiarity in terms of handling and ease of use.

Other software features include the ability to zoom in and out of the image and the ability for the digital system to use a means such as deep learning/artificial intelligence to identify pathology and alert the clinical user.

The viewing device may be any suitable device with a screen such as a tablet, lap top or desk top computer. The device may have a high definition screen. The viewing device can be located in a position that is comfortable for the clinical user to successfully carry out procedures.

Suitable illumination may be provided to the device of the invention as part of the camera or in addition to the camera.

The otoscope need not be provided with a handle. Unlike existing otoscopes this is not required and the clinician can simply hold the speculum when using the otoscope. A handle may be provided as part of the otoscope if required. The handle may be secured to the attachment means or may be provided with means to receive and secure to the speculum.

Applications

According to the second aspect, the present invention provides a method of using a device according to the first aspect. In this method the attachment means may be secured to the first end of the speculum by the attachment portion. The camera may be inserted into the portion to receive the camera or may be provided already in place.

The camera may be placed in the first position such that it can view a region beyond the second opening of the speculum.

The speculum may be held in the ear of the patient by the user and the ear canal may be viewed by the user through the camera and/or any viewing device provided.

If treatment using instruments is required the camera can provide suitable views of the ear canal during use of the instruments without restricting or preventing access for the instruments. Instruments can be inserted into the ear canal through the speculum without the need to move the camera away from the first position. The position and size of the camera and the attachment means allow sufficient access for instruments.

If treatment has resulted in the instruments being contaminated with ear wax or other foreign bodies the camera can be moved to the second position while the instruments are extracted to avoid contamination of the camera.

According to the third aspect, the present invention provides a method of diagnosing a disease or condition, the method comprising providing a device according to the first aspect and using the device in the process of diagnosing a disease or condition.

According to the fourth aspect, the present invention provides a method of treating a disease or condition, the method comprising providing a device according to the first aspect and using the device in the process of treating a disease or condition.

The disease or condition may include ear canal obstruction, otitis media, glue ear, swimmer's ear, tinnitus, Meniere's disease, otosclerosis, otomycosis, barotrauma, perichondritis, ruptured eardrum, presbycusis, cholesteatoma, hearing loss, or vestibular neuronitis.

The device may be an otoscope.

In a preferred embodiment, the otoscope is for use in aural microsuction.

The methods of the present invention may include the steps of: providing a device according to the first aspect, preferably an otoscope; providing an instrument; and/or removing ear wax or debris.

Instruments that may be used with an otoscope of the present invention include microsuction and/or tools, such as wax hooks and/or Jobson Horne Probes. The instruments may be elongate.

It will be understood that the instruments and methods of the present invention may be used for a human or for an animal that is not a human.

While described for the ear, it will be appreciated that the device of the present invention may be adapted for use to examine and/or treat other parts of a patient, for example the nose (e.g. anterior nose), mouth, eye, vagina, penis or anus. For example, the device of the present invention could be used for diagnosis, visualization, image recording, image sharing (such as in remote or telemedical care), the training of clinicians, or foreign body removal.

The proposed device may also be used for any other procedure that requires the passage of medical apparatus/instruments to perform a procedure.

DESCRIPTION OF THE DRAWINGS

An embodiment of the present invention will now be described with reference to the accompanying drawings, in which:

FIG. 1c is a perspective view of the otoscope as shown in FIG. 1a;

FIG. 2c is a perspective view of the otoscope as shown in FIG. 2a;

FIG. 3b is a side view of the otoscope as shown in FIG. 3a;

FIG. 3c is a side view of the otoscope shown in FIG. 3a, wherein the camera is in a second position;

FIG. 4a is a perspective view of an attachment means and a speculum;

FIG. 4b is a cross-section of the attachment means and speculum shown in FIG. 4a along a plane defined by a central axis of the speculum;

DETAILED DESCRIPTION

Figure 1A:
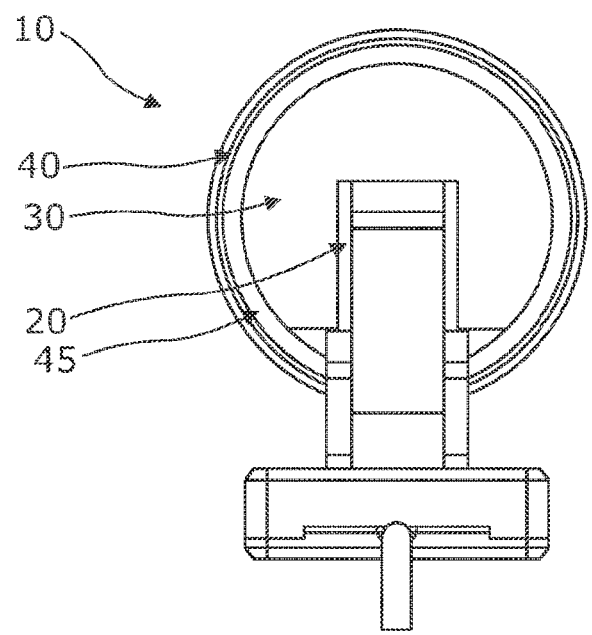
FIG. 1a is a view of an otoscope according to the present invention, wherein the camera is in a first position.

Referring firstly to FIGS. 1a to 1d of the accompanying drawings, an otoscope 10 according to the present invention is shown. The otoscope comprises a digital camera 20, an ear speculum 30 and an attachment means 40 for attaching the camera to the speculum.

The speculum defines a first end 32 with a circular first opening, and a second end 36 with a circular second opening. The first opening and the second opening are substantially parallel. The first opening defines a larger diameter than the second opening. The center of the first opening and the center of the second opening define a central axis. A curved side wall extends between the first opening and the second opening. The speculum is hollow and funnel-shaped.

The speculum shown in this non-limiting example is a commercially available speculum in which the diameter of the first opening is 43 mm and the diameter of the second opening is 35 mm.

The attachment means 40 is attached to the first end 32 of the speculum. The attachment means 40 comprises an attachment portion and a portion to receive the camera. The attachment portion comprises a ring 45 that is configured to fit within the first end of the speculum, i.e. within the first opening. The ring 45 press fits within the first end 32 of the speculum.

Figure 1B:
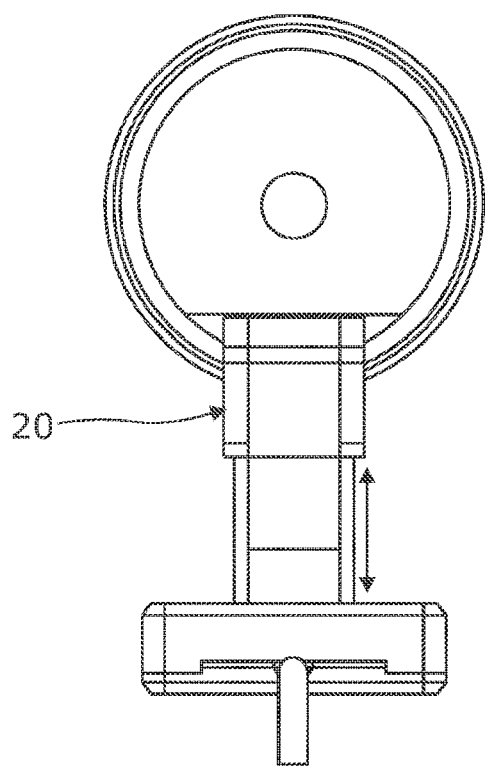
FIG. 1b is a view of the otoscope shown in FIG. 1a, wherein the camera is in a second position.
Figure 1C:
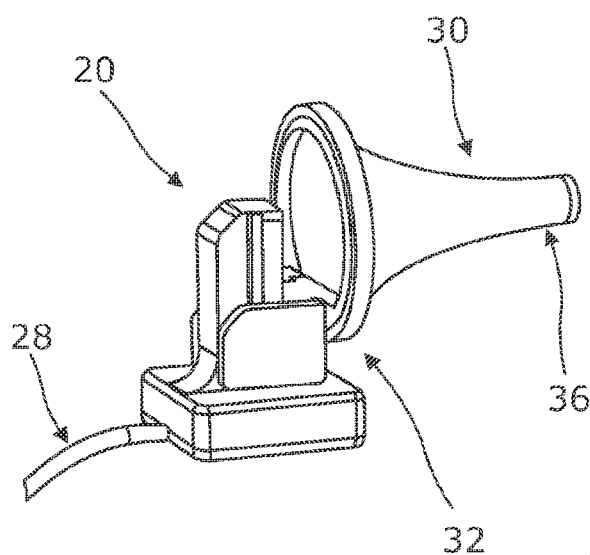
Figure 1D:
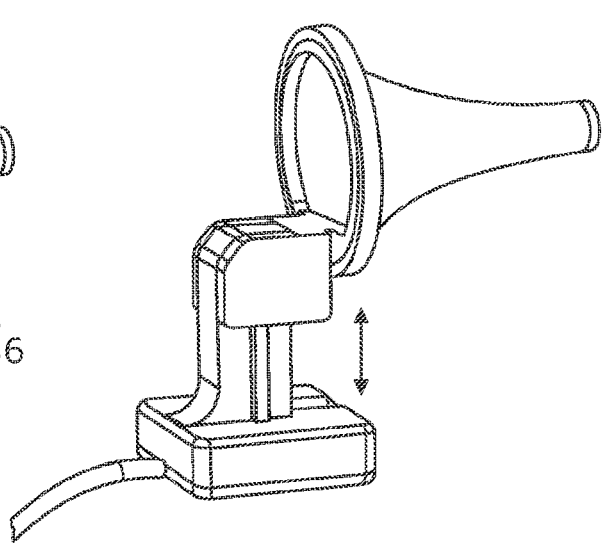
FIG. 1d perspective view of the otoscope as shown in FIG. 1b.

The portion to receive the camera is of unitary construction, therefore formed as one piece, with the attachment portion. The camera is movable within the portion to receive the camera. In FIG. 1a and FIG. 1c, the camera is shown in a first position in which the camera view is along the central axis of the speculum and it can view a region beyond the second opening. In FIG. 1b and FIG. 1d, the camera is shown in a second position in which it does not extend across the first opening at all. The portion to receive the camera is configured to allow the camera to be displaced from the first position in a plane that is perpendicular to the central axis or parallel to the plane of the first opening to the second position. The displacement is by means of the camera being slidably received by the portion to receive the camera such that it can slide between the first and second positions. The size, shape and configuration of the portion to receive the camera allows the movement and position of the camera to be controlled by pressure applied by the fingers of the clinician.

This displacement in particular reduces the risk of the camera being contaminated with earwax on an instrument as it is removed from the speculum.

The camera views a region beyond the second opening by viewing along the central axis from a position substantially in the plane of the first opening. The camera is positioned 10 mm or less outside of the plane of the first opening. The camera is connected to a viewing device, such as a tablet (not shown) by a cable 28.

A user of the otoscope shown in FIG. 1 could hold the otoscope by its speculum or attachment means, for example. FIG. 1 shows that no handle is present in this embodiment of the invention.

The otoscope is configured to allow an instrument to reach through the first opening and the second opening of the speculum such that the instrument can be operated by a user from beyond the first opening to operate in the region beyond the second opening.

FIGS. 2a to 2d of the accompanying drawings shows an otoscope 10 according to the present invention. The otoscope comprises a camera 20, a speculum 30 and an attachment means 40.

Figure 2A:
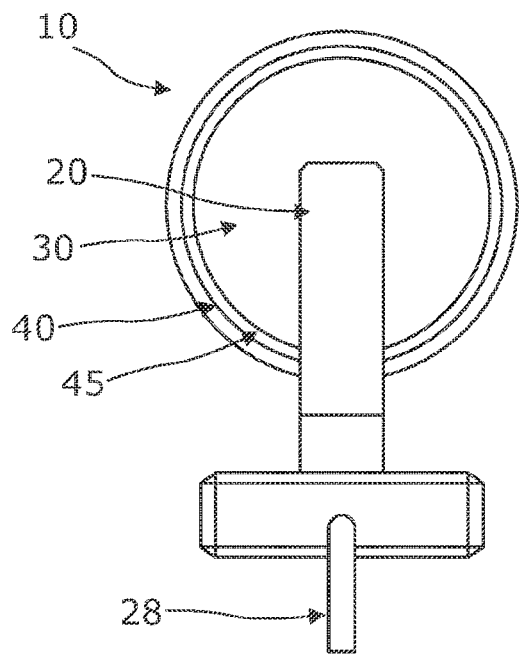
FIG. 2a is a view of an otoscope according to the present invention wherein the camera is in a first position.
Figure 2B:
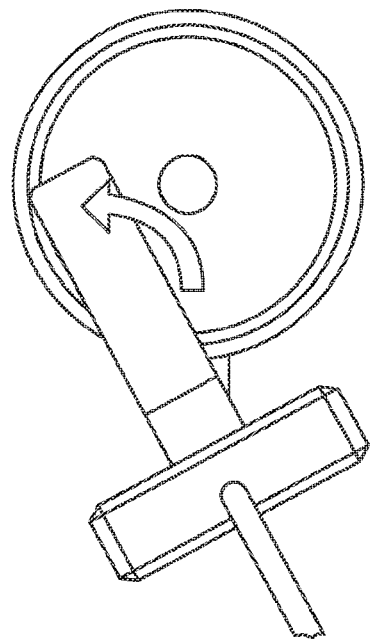
FIG. 2b is a view of the otoscope shown in FIG. 2a, wherein the camera is in a second position.
Figure 2C:
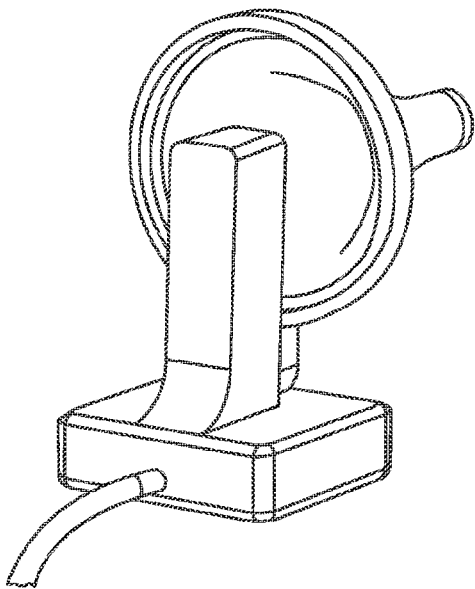
Figure 2D:
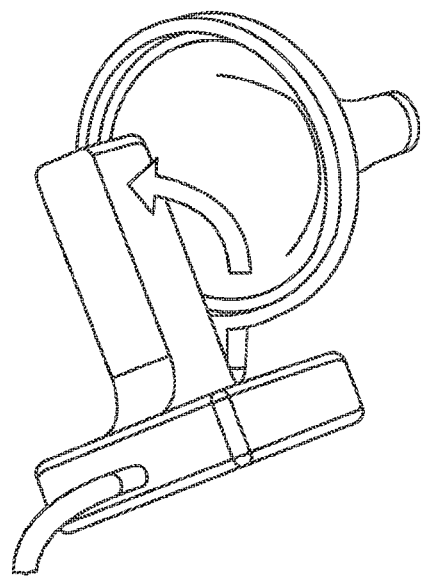
FIG. 2d is a perspective view of the otoscope as shown in FIG. 2b.

The speculum is similar to that shown in FIG. 1, and the attachment means 40 attaches to the first end of the speculum 30 by means of the attachment portion in the form of ring 45 as described in relation to FIG. 1. The attachment means also comprises a portion to receive the camera (not visible). In FIG. 2a and FIG. 2c, the camera is shown in a first position in which the camera view is along the central axis of the speculum such that it can view a region beyond the second opening. In FIG. 2b and FIG. 2d, the camera is shown in a second position in which it does not extend fully across the first opening. The portion that receives the camera is pivotally secured to the attachment means such that the camera can rotate or pivot between the first position and the second position.

The camera views a region beyond the second opening by viewing along the central axis from a position substantially in the plane of the first opening. The camera is positioned 10 mm or less outside of the plane of the first opening. The camera is connected to a viewing device, such as a tablet (not shown) by a cable 28.

Although not shown the portion to receive the camera can envelope the camera or have a portion that envelopes the camera. The portion to receive the camera can be or comprise a rectangular housing or "tower". The tower is preferably made a transparent material especially at the edge/face that directly faces the first end 32 of the speculum so that the light reflection back to the camera is unimpeded and the illumination system from any LED's is also unimpeded. The tower may have optical properties that allow the focusing of the illumination or the camera or both. The tower may also hold electronics to drive the individual components such as the camera. FIGS. 1a to 1d and FIGS. 3a to 3c show different orientations for the electronics.

Figure 3A:
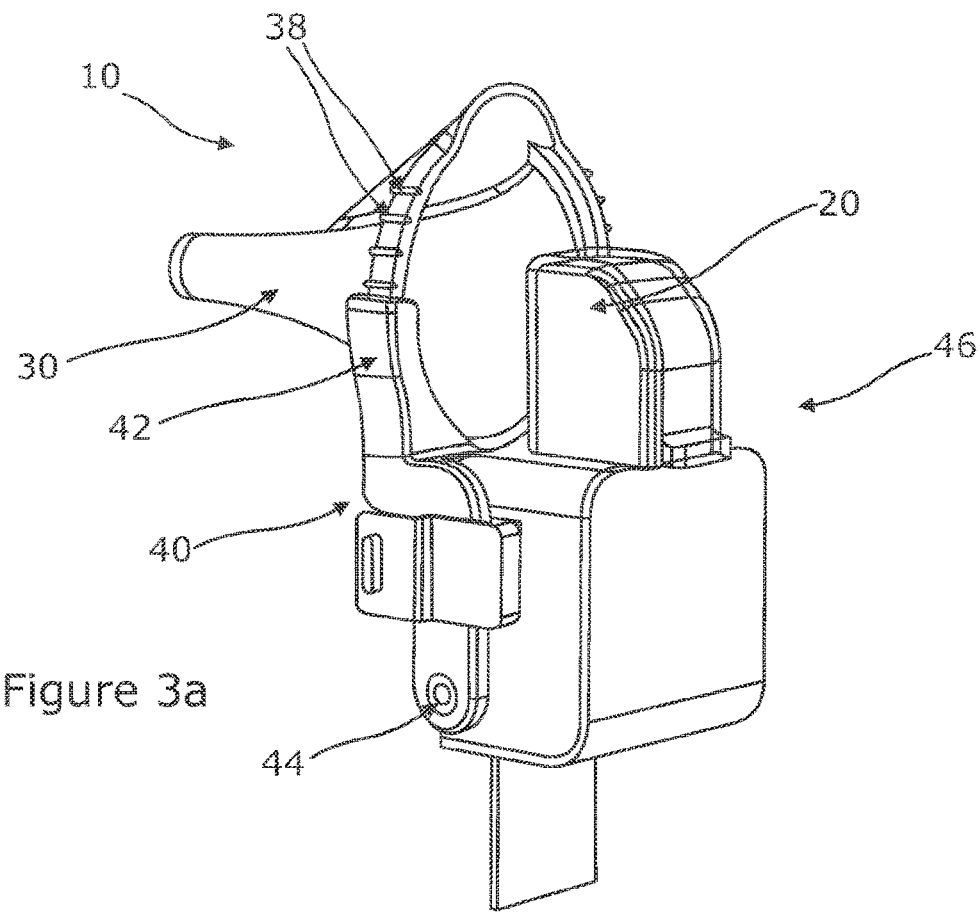
FIG. 3a is a perspective view of an otoscope according to the present invention, wherein the camera is in a first position.
Figure 3B:
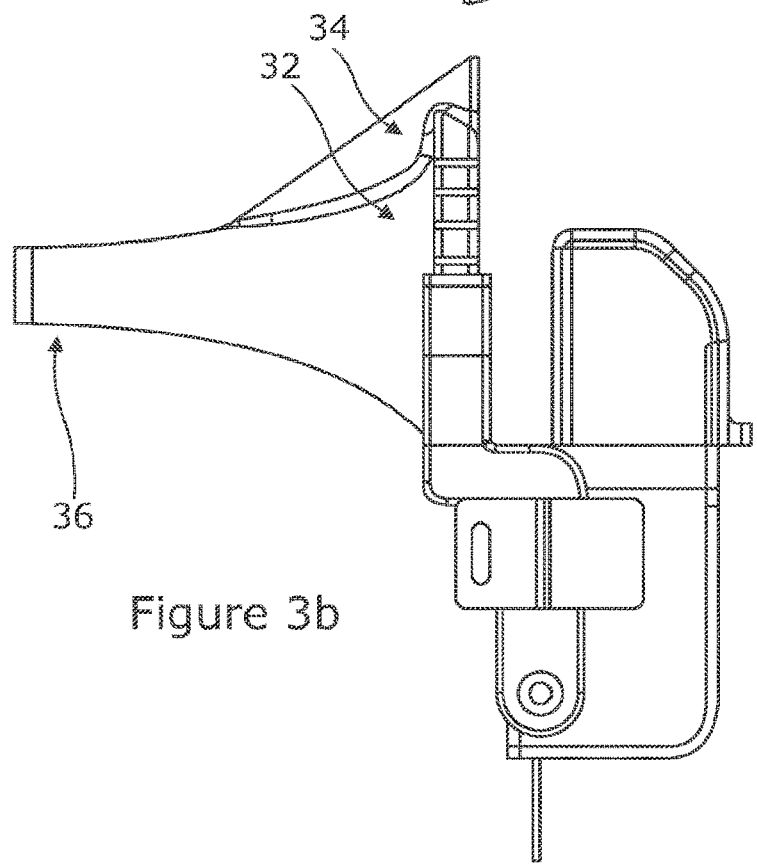
Figure 4C:
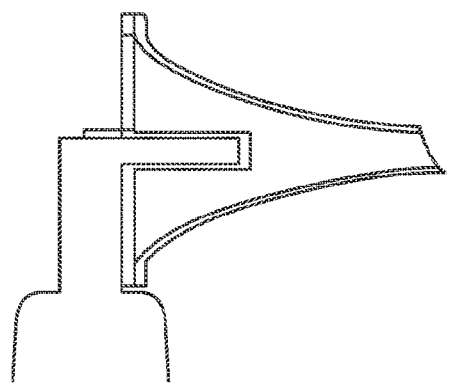
FIG. 4c is a cross-section of an otoscope along a plane defined by a central axis of the speculum.
Figure 4D:
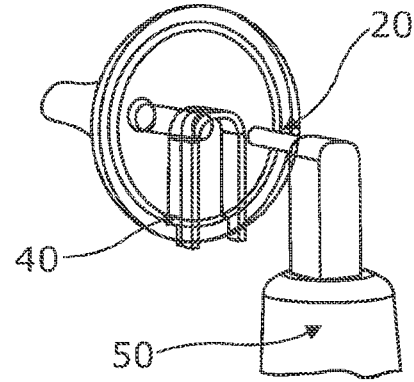
FIG. 4d is a rear perspective view of the otoscope shown in FIG. 4c, wherein the camera has been detached from the attachment means.

FIGS. 3a to 3c of the accompanying drawings shows an otoscope 10 according to the present invention. The otoscope comprises a camera 20, an ear speculum 30 and an attachment means 40.

The speculum defines a first end 32 with a projection 34. The projection extends from the first end approximately half way along the length of the speculum. The first end 32 has a first opening that is mostly circular, except for the projection 34 where the circumference of the first opening is expanded. The speculum also defines a second end 36 with a circular second opening.

The first opening and the second opening are substantially parallel. The first opening defines a larger diameter than the second opening. The centre of the first opening and the centre of the second opening define a central axis. A curved side wall extends between the first opening and the second opening. The speculum is hollow and funnel-shaped.

The attachment means comprises an attachment portion 42 for attachment to the first end of the speculum. The attachment portion 42 is adapted fit around a part of the first end of the speculum. The attachment portion 42 is configured to engage with ribs 38 on the external surface of the first end of the speculum, the ribs being elongate and parallel to the central axis. The attachment portion is arc shaped, the arc extends approximately 180° or more around the central axis of the speculum.

The attachment means further comprises an extension 44 extending from the attachment portion away from the speculum and being parallel to the plane of the arc of the attachment portion. The extension 44 comprises a hinge or pivot to attach to the portion 46 to receive the camera.

The portion to receive the camera is attached to the attachment portion through the hinge or pivot of portion 44. In FIG. 3a and FIG. 3b, the camera is shown in a first position in which the camera view is along the central axis of the speculum such that it can view a region beyond the second opening. In FIG. 3c, the camera is shown in a second position in which it does not extend across the first opening at all. The portion that receives the camera is secured to the attachment means by a hinge so that the camera can move between the first and second positions by a hinged movement. In this way, the otoscope is configured to allow the camera to be displaced from the detection position in a plane defined by the central axis or in a plane perpendicular to the first opening.

The camera of the otoscope shown in FIG. 3 communicates with a viewing device that is connected to the camera wirelessly. For example, the connection may be by Bluetooth or WiFi.

A further aspect of the embodiment in FIG. 3 is a mechanism that allows the speculum to be rotated while keeping the camera in a static position. This mechanism works through movable communication between the attachment portion 42 and ribs 38 on the outer surface of the speculum around the first opening. This sometimes may be necessary for the clinician to allow a better fit to an individual's curvature of their ear canal but keep the camera in a static position so stopping the camera picture from being rotated.

We also disclose a new type of ear speculum—where there is a bulge/protrusion/channel/tunnel that allows greater movement of surgical instruments and allows a greater distance of clearance away from the camera attachment means. Based on a clinician's dexterity—the speculum can be rotated so that the bulge/protrusion/channel/tunnel is same laterality of the hand that is using the medical instruments.

FIGS. 4a to 4d of the accompanying drawings shows an otoscope 10 according to the present invention. The otoscope also comprises an ear speculum 30. The plane of the second opening of the speculum is at an angle of about 30° from the angle of the plane of the first opening.

The otoscope comprises a camera 20 that extends beyond the plane of the first opening, into the speculum, by a distance of about 10-15 mm.

The otoscope comprises a handle 50 that is integral with or contains the camera. In use, a clinician will hold the handle. A cable to attach a viewing device to the camera extends from the handle.

The otoscope also comprises an attachment means 40. The attachment means comprises an attachment portion in the form of a ring 45 that fits within the first end of the speculum.

The portion that receives the camera is fixed to or unitary with the attachment portion. The portion that receives the camera comprises an elongate mount 47 that extends radially from the attachment portion towards the centre of the first opening and a tubular portion 48 extending therefrom perpendicular to the elongate mount in which the camera can be press fit. As such as the ways to move the camera relative to the speculum are to either detach the camera or detach the speculum from the attachment means. The camera detects along the central axis to allow the best possible view of the ear canal for the clinician.

FIG. 4b shows a cross-section through the speculum and attachment means. The line A-A shows the central axis of the speculum. It can be seen that, in use, the attachment means will align the camera to detect along the central axis of the speculum. This gives the best possible view of the ear canal for the clinician.

FIG. 5 is the side profile a new type of ear specula, which has an extension to receive a micro digital camera system. FIG. 5a shows a camera system at the mouth of the speculum and is flush to the same vertical axis specula mouth. Annotation 1 refers to the tip of the speculum that enters the patient first. Annotation 2 refers to built in recess that holds the camera, lighting parts. Annotation 4 refers to wires of the camera. FIG. 5c refers to the structure of annotation 2, which has openings+/−focusing lenses that allow a light source e.g. a white LED source (but not limited to that) and opening for the camera. The camera portion ends at central point of the ear specula to allow co-axial views of the tympanic membrane. FIG. 5b shows an alternative embodiment of this speculum. In this embodiment there is an additional horizontal strut (annotation 3) that places the camera structure away from the mouth. The reason for this is that being further away from the mouth of the camera may mean the camera is not contaminated by wax and other ear canal debris.

The strut would be of a short length so that the camera view would not be obscured by hand.

In all embodiments, the camera is attached by wire to a high definition display such as a tablet and the wire transmits the electronic signals from the camera to the tablet. We envisage the tablet, power electronics and power management systems will be in portable stand, which can be based by the patient and then a swivel arms which connects the tablet and the stand can be provide rotation of the display depending if the practitioner is performing a procedure in the left or right ear.

Software within the display and will manipulate the image to provide clear natural colour image. Software and the camera can be manipulated for zoom functions of the product. Software can also perform real-time/live or historical data analysis to inform the clinical user of normal and abnormal pathology.

We do not wish to limit our electronic transmission to just wires, but this can be done without wires with WiFi or Bluetooth technologies but not limited to just those technologies.

Figure 5A:
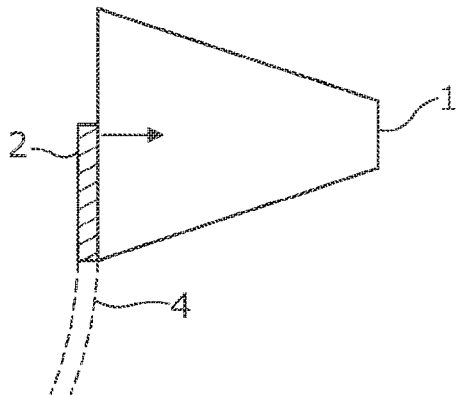
FIGS. 5-10 are views of otoscopes according to the present invention.
Figure 5B:
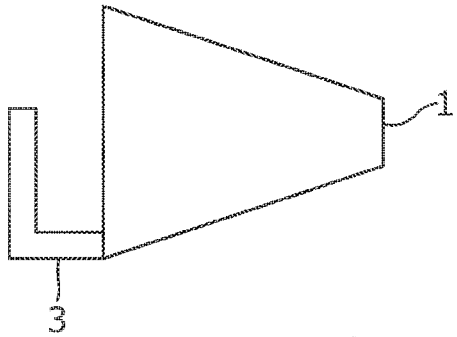
Figure 5C:
Figure 5D:
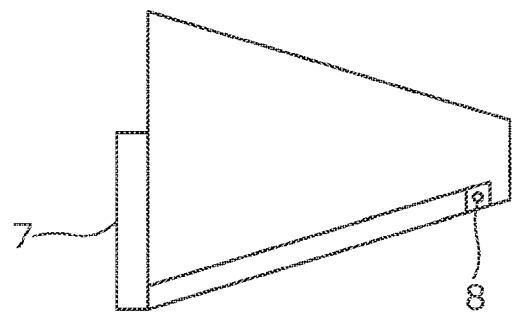

FIG. 5d shows a possible embodiment of the ear speculum is to have an opening that leads to a tunnel (annotation 7) along the inner side of the speculum—which acts as a port for a flexible microcamera. The tunnel would protect the microcamera from any debris and dirt and would have at the end, a clear covering which may also act as a focusing lens (annotation 8). The end of the tunnel can end at the tip of the speculum or just before. The reason to add such a port is that a flexible camera at the end of the tip increases the field of view an otoscope can be used as a screening tool.

Figure 6:
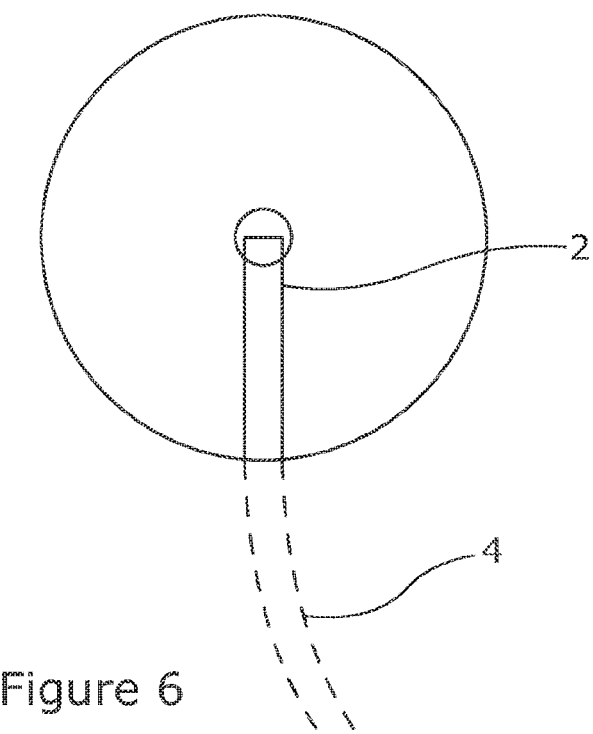

FIG. 6 is view of the camera from the opening side. FIG. 6 is a view of the camera from the first opening side. In the preferred embodiment, the camera and lighting system only take a small proportion of the total surface area of the south. In this figure, the camera is at a 6 o'clock position however in this position instruments would find the passage of instruments to be obstructive. Because aural microsuction (AM) is an ambidextrous procedure, we envisage that the camera can be held at 8 o'clock and 4 o'clock positions. In these positions, it allows para-central insertion of instruments. When the camera is in these positions, software and hardware can re-orientate the image to the user. These positions are for example and are not limiting on possible positions.

Though the speculum can be simply rotated in the hand to these positions, an alternative embodiment is to have within the outer ring of the ear speculum the camera system along an inner track, which can be rotated. This would also allow for the camera to be fixed in position.

Avoiding Wax Contamination

Figure 7A:
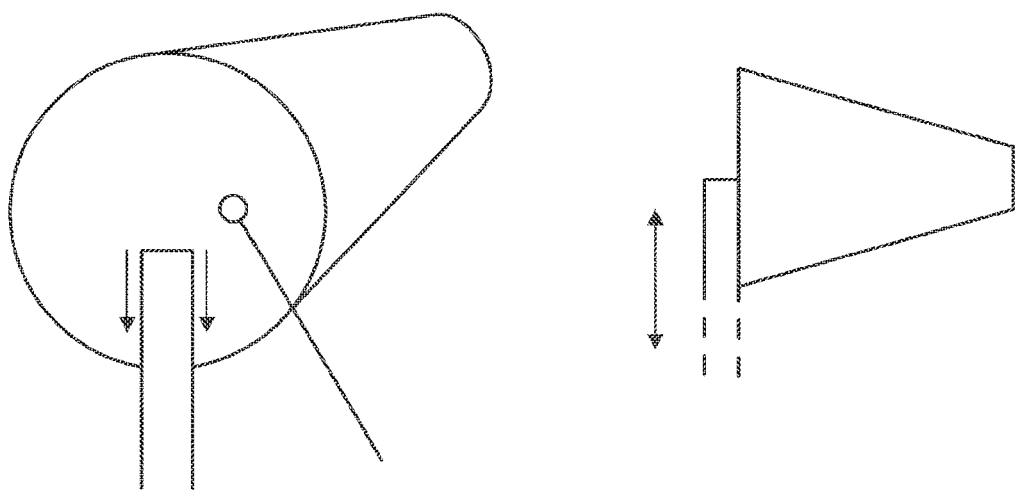
Figure 7B:
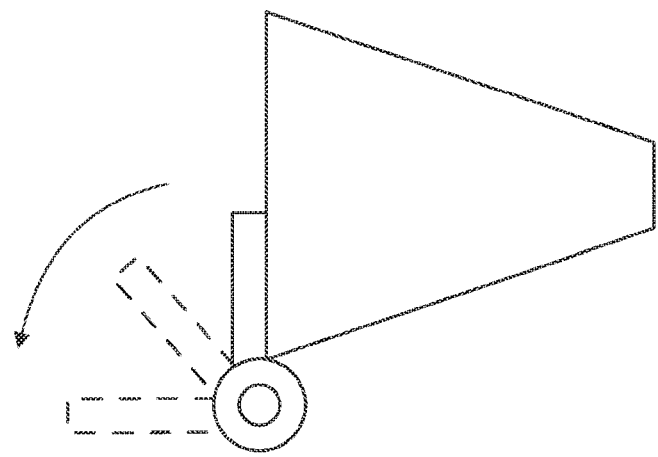
Figure 7C:
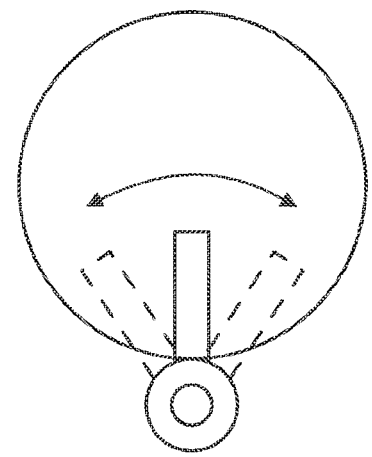
Figure 7D:
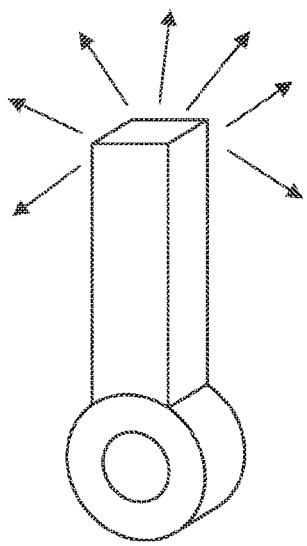

In FIGS. 7a-c we describe mechanisms to move the camera out of the way when surgical instruments are removed. There is a risk that when instruments are removed with wax and other ear debris, on the extraction of these instruments—the wax and debris can contaminate and cover the camera system. There also may be a mechanism (e.g. ratchet) that allows the camera to be retracted nearer and further to the specula end tip as required.

FIG. 7a: An alternative embodiment of a mechanism to avoid earwax contamination on the camera system is to have a mechanism that allows the camera to be moved downwards such as using a spring loaded mechanism. During AM, specula are held in the hand with the thumb, index and middle finger. In this embodiment preserves this natural hold of the specula, since the index finger can rest on the camera system. When a large piece of wax cerumen or debris is removed, it's envisaged that the finger can press down on the camera system to push it out of the way and avoid wax contamination with the camera. When the camera is needed, the mechanism can be released to allow restoration of the camera to the neutral position. It's also envisaged that camera when it's pressed down goes into a recess as part of the speculum or as in built on the camera attachment mechanism or part of the camera setup.

Figure 7E:
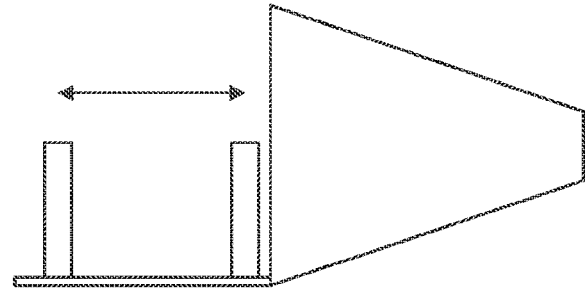

FIG. 7e shows a possible mechanism and embodiment of moving the camera out of the way. In this embodiment the camera holding element is on a track. The camera and the holding element can be moved along the track with the use of finger. There is also be a form of locking mechanism that keeps the camera in the position and the locking mechanism is disengaged when the camera is required to be move along the track. The track is intended to be along the horizontal axis in parallel to how the speculum is inserted into the ear.

FIG. 7b shows another possible embodiment of an avoidance mechanism. In this mechanism the camera can be moved out of position by having the camera rotate on an axis. Again the camera would be locked in position but the use of a finger or electronic/mechanical button would allow the camera to swing out of the way. The camera would have predominantly two axis's could rotate, in FIG. 7b the camera in a vertical motion so the camera can be "flipped down" in FIG. 7c, the motion is horizontal. Finally FIG. 3D represents a camera mounted on a spherical/ball structure which allows 360 multidirectional movement. We also anticipate a combination of mechanisms may also be available as well.

In addition—it is an ambition of the embodiment that if necessary the tower and parts of the speculum can be cleaned with an anti-infective anti smear wipe/spray especially areas that may obscure the camera part.

Though in this application we describe aural microsuction as the primary purpose, there are many other possible specula that our camera system can be fitted with for example with nasal specula, which would allow direct visualization of the anterior part of the nose in the management of nose bleeds.

Figure 8:
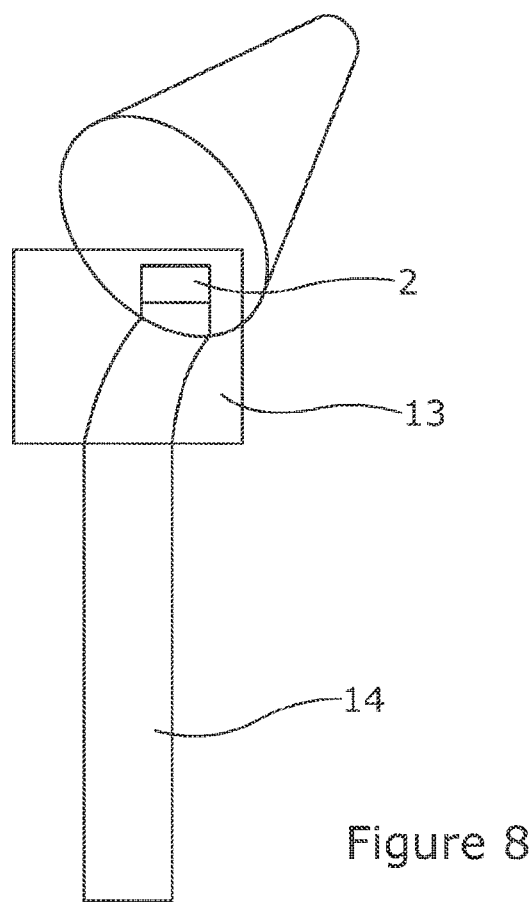

FIG. 8 describes an embodiment with a handle (annotation 14); which has the electronics and batteries. Annotation 13 is display integrated into the embodiment. The display would pick up signals from the camera system (annotation 2). Within the handle may be buttons that activate mechanisms described in FIG. 7 about removing the camera out of the way.

Figures 9A, 9B:
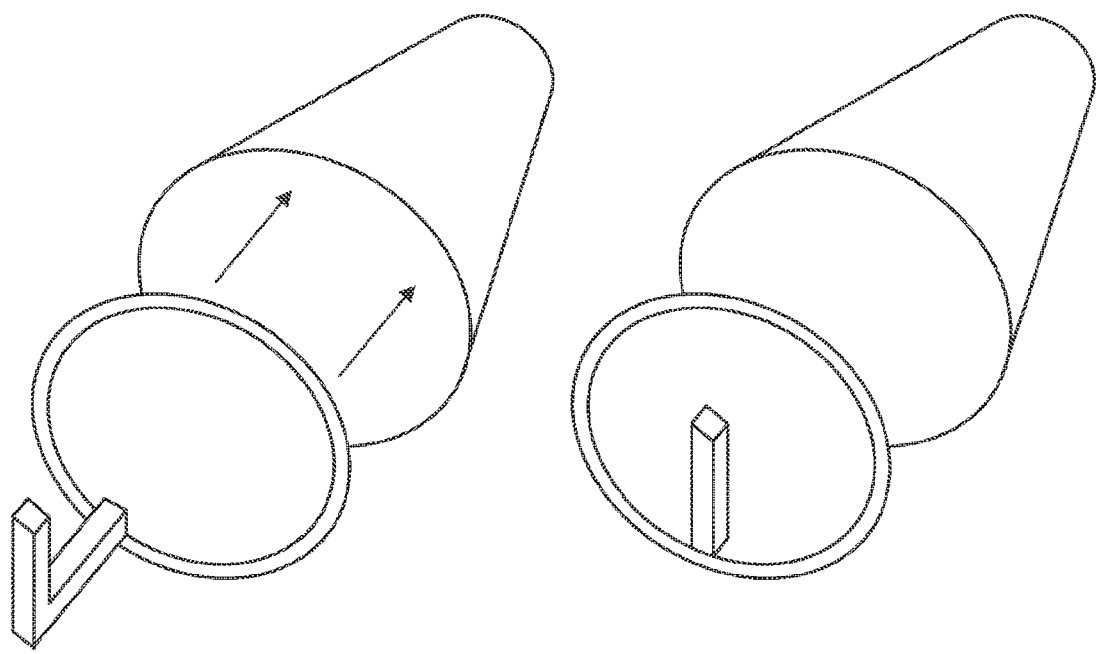

FIG. 9 describes a construction that a single ring and camera. The purpose of this system is that it would allow the digital camera system to be retrofitted into any ear specula and by allowing the hand to hold specula, creates a digital otoscope system.

Figure 10:
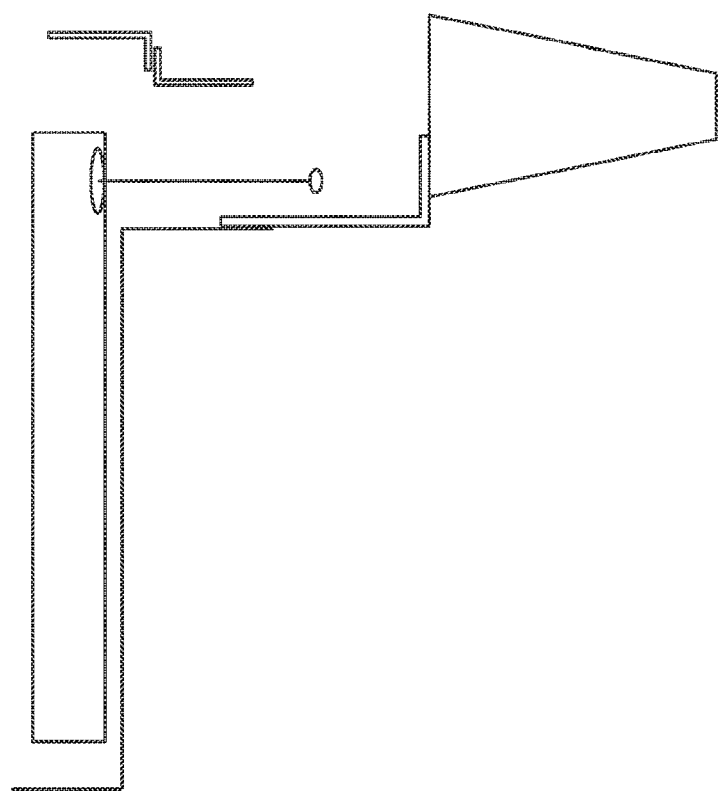

FIG. 10 describes an embodiment using a smartphone/portable device, which the portable device camera is located with a gap between the specula and the mobile device to allow the passage of instruments. Previous smartphone otoscopes all have enclosed systems which do not allow the passage of instruments.

Because of the limitations of the digital systems, compared to ear microscopes, we also envisage that the speculum can be made of a transparent material; which can aid in the "anatomical mapping" that AM practitioners do. This would allow a greater field of view that endoscope systems allow.

One of the limitations of digital systems is that with single cameras only allow 2D planar view. We would also describe a system where a plurality of cameras may be present, and by having a plurality allows a 3D dimensional view of the outer ear canal.

Other functions include:
A chip system on the specula so that when the camera attaches; there is an automatic recognition of which specula is being used and software will be at the right settings.
Within the walls of the specula—with space permitting there can be channels which allow the passage of instruments (rather than through the speculum) such as water channels, pneumatic air.

The invention claimed is:

1. A device comprising a digital camera, a speculum and an attachment means for attaching the camera to the speculum, wherein:
the speculum defines a first end with a first opening, and a second end with a second opening, such that there is a through channel from the first opening through the second opening, and wherein the attachment means comprises a portion to receive the camera and is configured to receive the camera such that the speculum is pivotally or rotatably secured to the attachment means while allowing the speculum to rotate or pivot while the camera remains in a static position;
the camera is configured to have a first position substantially in the plane of the first opening such that the camera can be used to view a region beyond the second opening and a second position in which the camera extends partly, across the first opening, wherein when the camera is in the second position the camera is not positioned to view along the central axis, wherein the portion to receive the camera is pivotally or rotatably secured to the attachment portion such that the camera can rotate or pivot between the first and second positions; and
the device is configured to allow an instrument to reach through the first opening and the second opening of the speculum such that the instrument can be operated by a user from beyond the first opening to operate in the region beyond the second opening with the camera in the first position while viewing the region beyond the second opening.

2. The device according to claim 1, wherein the centre of the first opening and the centre of the second opening of the speculum define a central axis, and wherein in the first position the camera can view a region beyond the second opening by viewing along the central axis from a position substantially in the plane of the first opening.

3. The device according to claim 1, wherein the speculum is an ear speculum.

4. The device according to claim 1, wherein the device is configured to allow the camera to be displaced from the first position in a plane that is perpendicular to the central axis or parallel to the first opening.

5. The device according to claim 1, wherein the device is configured to allow the camera to be displaced from the first position in a plane defined by the central axis or in a plane perpendicular to the first opening.

6. The device according to claim 1, wherein the attachment means comprises an attachment portion for attachment to the first end of the speculum.

7. The device according to claim 6 wherein the attachment portion comprises a ring adapted fit around the first end of the speculum or fit within the first end of the speculum.

8. The device according to claim 1, wherein the camera is movable within the portion to receive the camera.

9. The device of claim 1, wherein the portion to receive the camera envelopes the camera or has a portion that envelopes the camera.

10. The device according to claim 9, wherein the portion to receive the camera includes a rectangular housing, and wherein at least part of the rectangular housing is made from a transparent material.

11. The device according to claim 1, wherein
a) when the camera is in the first position, the camera is 40 mm or less, 30 mm or less, 20 mm or less, or 10 mm or less, or 5 mm or less, or 4 mm or less, or 3 mm or less, or 2 mm or less, or 1 mm or less either inside or outside of the plane of the first opening; or
b) when the camera is in the first position, the camera is in the plane of the first opening.

12. The device according to claim 1, wherein any one or more of the following applies:
a) the camera is a digital microcamera;
b) one or more lenses are provided in front of the camera; and
c) a lighting system is provided.

13. The device according to claim 1, wherein the device is an otoscope.

* * * * *